(12) United States Patent
Hanna et al.

(10) Patent No.: US 6,720,039 B1
(45) Date of Patent: Apr. 13, 2004

(54) LIQUID CRYSTALLINE COMPOUNDS AND PROCESS FOR PRODUCING THE SAME

(75) Inventors: Junichi Hanna, Shinjuku-Ku (JP); Masahiro Funahashi, Shinjuki-Ku (JP); Komei Kafuku, Shinjuku-Ku (JP); Kyoko Kogo, Shinjuki-Ku (JP)

(73) Assignee: Dai Nippon Printing Co., Ltd. (JP)

( * ) Notice: Subject to any disclaimer, the term of this patent is extended or adjusted under 35 U.S.C. 154(b) by 0 days.

(21) Appl. No.: 09/679,538

(22) Filed: Oct. 6, 2000

Related U.S. Application Data

(62) Division of application No. 09/025,249, filed on Feb. 18, 1998, now Pat. No. 6,174,455.

(30) Foreign Application Priority Data

Feb. 19, 1997 (JP) ................................................ 9/49593

(51) Int. Cl.$^7$ .................. C09K 19/32; C00K 19/58; C07C 13/48; G03G 5/06; G02F 1/13
(52) U.S. Cl. ................ 428/1.1; 252/299.3; 252/299.62; 252/501.1; 560/56; 560/100; 585/410; 257/59; 430/56; 430/58.05; 349/69
(58) Field of Search ........................... 252/299.3, 501.1; 560/56, 100; 585/410; 349/2, 69; 430/58.05; 257/40, 59, E51.049

(56) References Cited

U.S. PATENT DOCUMENTS

| | | | |
|---|---|---|---|
| 4,386,007 A | 5/1983 | Krause et al. .......... 252/299.62 |
| 5,072,021 A | 12/1991 | Nakatsuka et al. ............ 560/56 |
| 5,143,644 A * | 9/1992 | Yamaoka et al. ....... 252/299.62 |
| 5,252,253 A | 10/1993 | Gray et al. ............. 252/299.62 |
| 5,589,103 A | 12/1996 | Yamada et al. ........ 252/299.61 |
| 5,698,740 A | 12/1997 | Enokida et al. ............. 564/308 |
| 5,766,510 A | 6/1998 | Hanna et al. .......... 252/299.62 |
| 6,174,455 B1 * | 1/2001 | Hanna et al. .......... 252/299.62 |
| 6,224,787 B1 * | 5/2001 | Hanna et al. ............. 252/299.3 |

FOREIGN PATENT DOCUMENTS

| | | |
|---|---|---|
| DE | 38 37 208 A1 | 5/1989 |
| DE | 41 16 158 A1 | 11/1992 |
| EP | 341922 | 11/1989 |
| EP | 517498 | 12/1992 |
| EP | 517 498 A1 | 12/1992 |
| EP | 518 636 A1 | 12/1992 |
| EP | 757 032 A2 | 2/1997 |
| FR | 2 551 561 | 3/1985 |
| GB | 1 603 075 | 11/1981 |
| JP | 8-109145 | 4/1996 |
| WO | WO 87/06577 | 11/1987 |
| WO | WO 90/08119 | 7/1990 |
| WO | 90/08119 | 7/1990 |
| WO | WO 95/04306 | 2/1995 |

OTHER PUBLICATIONS

Hird et al., "Palladium–catalysed cross–coupling reactions in the synthesis of some high polarizability materials", Liquid Crystals, 1993, vol. 14, No. 3, pp. 741–761.*

Kato, T. et al. "Solid–state CP/MAS carbon–13 NMR studies of naphthalene–based thermotropic polyesters and model compounds", J. Polym. Sci. Part A: Polym. Chem, 1989, vol. 27 pp. 1447–1465 XP002103112.

Chemical Abstracts, vol. 120, No. 26, Jun. 27, 1994, Columbus, Ohio Abstract No. 335199, Sato et al., "Liquid Crystal Naphthalene Compound and its Composition for Display" XP002103115 Abstract & JP 06 025061.

Gaetano Aloisi et al. "Triplet and radical ion properties of styrylnaphthalenes and their aza–derivatives: a laser flash photolytic study", J. Chem. Soc., Faraday Trans. 1992, vol. 88 pp. 2139–2145 XP002103113 pp. 2139–2145.

Wong et al. "Novel approach in molecular design for quadratic nonlinear optics (NLO): Design, syntheses and characterizations of new classes of dipolar and multi–dipolar molecules" MCLC S&T, Sect. B: Nonlinear Opt, 1995, vol. 9 pp. 181–186, XP002103114.

Funahashi et al. "Fast ambipolar carrier transport in smectic phases of phenylnaphthalene liquid crystal" Applied Physics Letters, vol. 71, No. 5, Aug. 4, 1997, pp. 602–604, XP000699625.

* cited by examiner

*Primary Examiner*—Shean C. Wu
(74) *Attorney, Agent, or Firm*—Parkhurst & Wendel, L.L.P.

(57) ABSTRACT

A liquid crystalline compound having a novel structure and a process for producing the same are provided. The liquid crystalline compound is represented by the following general formula (I):

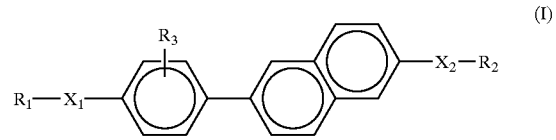

(I)

wherein $R_1$ and $R_2$ each independently represent a straight-chain, branched or cyclic, saturated or unsaturated hydrocarbon group having 1 to 22 carbon atoms and may be attached directly to the aromatic ring without through $X_1$ or $X_2$; $R_3$ represents a hydrogen atom, a cyano group, a nitro group, a fluorine atom, or a methyl group; and $X_1$ and $X_2$ each independently represent an oxygen atom, a sulfur atom, or a —CO—, —OCO—, —COO—, —N=CH—, —CONH—, —NH—, —NHCO—, or —CH$_2$— group.

13 Claims, No Drawings

LIQUID CRYSTALLINE COMPOUNDS AND PROCESS FOR PRODUCING THE SAME

This is a Division of application Ser. No. 09/025,249 filed Feb. 18, 1998 U.S. Pat. No. 6,174,455.

BACKGROUND OF THE INVENTION

The present invention relates to liquid crystalline compounds and more particularly to novel crystalline compounds, which exhibit liquid crystallinity and, in addition, charge transport capability, and a process for producing the same.

Liquid crystalline compounds having various structures are known in the art and are widely used mainly as materials for information display devices using an electro-optic effect based on the alignment effect of liquid crystal molecules attained by application of voltage. Further, application of liquid crystalline compounds to optical shutters, optical stops, modulating devices, lenses, light beam deflection/optical switches, phase diffraction gratings, optical logic devices, memory devices and the like are under study. External simulation by heat, electric field, magnetic field, pressure or the like results in transition of the alignment of liquid crystal molecules which enables optical properties and electric capacity to be easily changed. Sensors and measuring instruments, utilizing this property, for temperature, electric field/voltage, infrared radiation, ultrasonic wave, flow rate/acceleration, gas or pressure have been studied in the art.

DISCLOSURE OF THE INVENTION

An object of the present invention is to provide liquid crystalline compounds having a novel structure and a process for producing the same.

The above object can be attained by the following present invention. Specifically, according to one aspect of the present invention, there is provided a liquid crystalline compound represented by the following general formula (I):

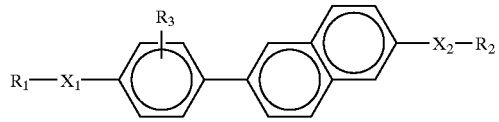

(I)

wherein $R_1$ and $R_2$ each independently represent a straight-chain, branched or cyclic, saturated or unsaturated hydrocarbon group having 1 to 22 carbon atoms and may be attached directly to the aromatic ring without through $X_1$ or $X_2$; $R_3$ represents a hydrogen atom, a cyano group, a nitro group, a fluorine atom, or a methyl group; and $X_1$ and $X_2$ each independently represent an oxygen atom, a sulfur atom, or a —CO—, —OCO—, —COO—, —N=CH—, —CONH—, —NH—, —NHCO—, or —CH$_2$— group.

According to another aspect of the present invention, there is provided a liquid crystalline compound represented by the following general formula (II):

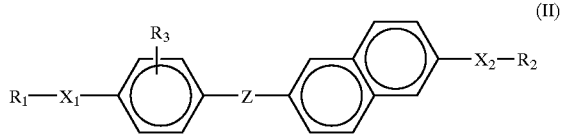

(II)

wherein $R_1$ and $R_2$ each independently represent a straight-chain, branched or cyclic, saturated or unsaturated hydrocarbon group having 1 to 22 carbon atoms and may be attached directly to the aromatic ring without through $X_1$ or $X_2$; $R_3$ represents a hydrogen atom, a cyano group, a nitro group, a fluorine atom, or a methyl group; $X_1$ and $X_2$ each independently represent an oxygen atom, a sulfur atom, or a —CO—, —OCO—, —COO—, —N=CH—, —CONH—, —NH—, —NHCO—, or —CH$_2$— group; and Z represents a —COO—, —OCO—, —N=N—, —CH=N—, —CH$_2$S—, —CH=CH—, or —C≡C— group.

According to still another aspect of the present invention, there is provided a process for producing the liquid crystalline compound represented by the general formula (I), comprising the step of reacting a compound represented by the following general formula (1) with a compound represented by the following general formula (2):

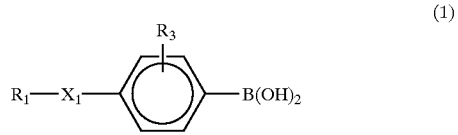

(1)

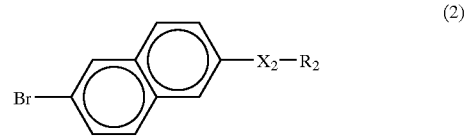

(2)

wherein $R_1$, $R_2$, $R_3$, $X_1$, and $X_2$ are as defined above.

According to a further aspect of the present invention, there is provided a process for producing the liquid crystalline compound represented by the general formula (II), comprising the step of reacting a compound represented by the following general formula (3) with a compound represented by the following general formula (4):

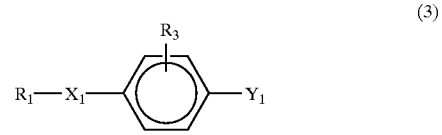

(3)

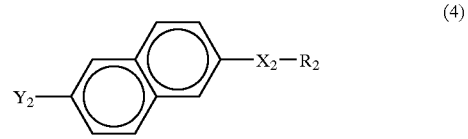

(4)

wherein $R_1$, $R_2$, $R_3$, $X_1$, and $X_2$ are as defined above; and $Y_1$ and $Y_2$ are respectively groups which are reacted with each other to form a —COO—, —OCO—, —N=N—, —CH=N—, —CH$_2$S—, —CH=CH—, or —C≡C— group.

The present invention can provide novel liquid crystalline compounds having not only liquid crystallinity but also charge transport capability. The novel liquid crystalline compounds can be used in applications, where the conventional liquid crystalline compounds are used, and, in addition, are useful as materials for optical sensors, electroluminescence devices, photoconductors, space light modulating devices, thin film transistors, other sensors and the like, utilizing the charge transfer capability. In particular, some of the liquid crystalline compounds of the present invention have both electron transport capability and hole transport capability and, when mixed with a fluorescent material in order to use them as a material for an electroluminescence device, can provide luminescence.

The present invention will be described in more detail with reference to the following preferred embodiments.

EXAMPLE 1

50 ml of THF (tetrahydrofuran) was added to 2.91 g (0.12 mol) of metallic magnesium, and the mixture was stirred. 100 ml of a solution of 26.89 g (0.1 mol) of p-octylbromobenzene in THF was added dropwise thereto, and the mixture was heated. After the initiation of the reaction was confirmed, the mixture was refluxed for one hr. The mixture was cooled to −78° C., 12.46 g (0.12 mol) of trimethylboric acid was added dropwise thereto, and the mixture was stirred for 30 min. The temperature was returned to room temperature, followed by stirring for additional one hr. Dilute hydrochloric acid was added thereto, and the mixture was stirred for one hr. The aqueous layer was extracted with ether, and the oil layer was washed with water and then with an aqueous sodium hydrogencarbonate. The oil layer was then dried over sodium sulfate, the solvent was removed by distillation, and the resultant crude product was purified by chromatography on silica gel to give p-octylphenylboric acid.

The above compound exhibited the following peaks in NMR spectrum:

$^1$H NMR (CDCl$_3$)

δ=8.14 (2H, d, J=8.6 Hz), 7.31 (2H, d, J=7.9 Hz), 2.68 (2H, t, J=7.3 Hz), 1.50–1.80 (4H, m), 1.20–1.40 (8H, m), 0.88 (3H, t, J=7.6 Hz)

22.29 g (0.1 mol) of 2-bromo-6-naphthol, 11.22 g (0.2 mol) of potassium hydroxide, and 32.36 g (0.13 mol) of 1-bromododecane were dissolved in ethanol (300 ml), and the solution was refluxed for 8 hr. Thereafter, water was added thereto, the mixture was cooled, and the resultant precipitate was collected by filtration and washed with a sodium hydroxide solution and then with water. The crude product thus obtained was recrystallized from ethyl acetate to give 2-bromo-6-dodecyloxynaphthalene.

The above compound exhibited the following peaks in NMR spectrum:

$^1$H NMR (CDCl$_3$)

δ=7.89 (1H, d, J=2.0 Hz), 7.62 (1H, d, J=8.9 Hz), 7.57 (1H, d, J=8.9 Hz), 7.47 (1H, dd, J1=2.0 Hz, J2=8.9 Hz), 7.15 (1H, dd, J1=2.6 Hz, J2=8.9 Hz), 7.07 (1H, d, J=2.6 Hz), 4.04 (2H, t, J=6.6 Hz), 1.84 (2H, quint, J=6.6 Hz), 1.40–1.50 (4H, m), 1.17–1.40 (14H, m), 0.88 (3H, t, J=6.8 Hz)

2.01 g (0.01 mol) of p-octylphenylboric acid, 3.91 g (0.01 mol) of 2-bromo-6-dodecyloxynaphthalene, and Pd(PPh$_3$)$_4$ (0.0005 mol) were dissolved in dimethoxyethane (50 ml), a 10% aqueous potassium carbonate solution (40 ml) was added thereto, and the mixture was refluxed for one hr. After cooling, the resultant precipitate was collected by filtration and washed with water and ethanol. The crude product thus obtained was recrystallized from hexane to give a compound represented by the following formula:

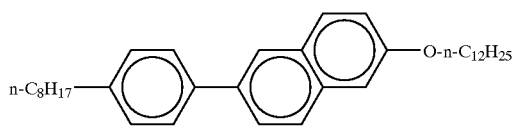

The above compound exhibited the following peaks in NMR spectrum:

$^1$H NMR (CDCl$_3$)

δ=7.94 (1H, d, J=1.3 Hz), 7.77 (2H, d, J=8.6 Hz), 7.69 (1H, dd, J1=1.7 Hz, J2=8.6 Hz), 7.62 (2H, d, J=8.3 Hz), 7.28 (2H, d, J=8.3 Hz), 7.16 (1H, dd, J1=2.6 Hz, J2=8.3 Hz), 7.14 (1H, s), 4.08 (2H, t, J=6.6 Hz), 2.66 (2H, t, J=7.3 Hz), 1.86 (2H, quint, J=6.8 Hz), 1.40–1.70 (4H, m), 1.20–1.70 (26H, m), 0.89 (3H, t, J=5.6 Hz), 0.88 (3H, t, J=6.9 Hz)

The above compound had the following phase transition temperatures.

Crystal—79.3° C.—SmX$_1$—100.4° C.—SmX$_2$—121.3° C.—Iso. (X$_1$ and X$_2$ were unidentified)

The charge mobility of the above compound was 10$^{-3}$ cm$^2$/Vs for both electron and hole.

EXAMPLE 2

2.18 g (0.01 mol) of p-octylbenzaldehyde and 3.28 g (0.01 mol) of 2-amino-6-dodecyloxynaphthalene were dissolved in ethanol (30 ml), and the solution was heated at 70° C. for 2 hr with stirring. After the reaction, the mixture was cooled to room temperature, and the precipitated solid was collected by filtration and recrystallized from ethanol to give a compound represented by the following formula. This compound had the same properties as the compound prepared in Example 1.

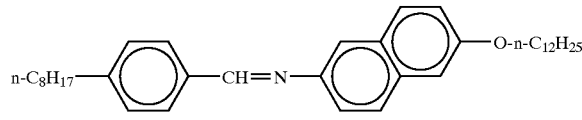

EXAMPLE 3

The procedure of Example 1 was repeated to prepare liquid crystalline compounds represented by the general formula (I) wherein R$_1$, R$_2$, R$_3$, X$_1$, and X$_2$ represent respective groups specified in Table 1. All the liquid crystalline compounds thus obtained had the same properties as the liquid crystalline compound prepared in Example 1.

TABLE 1

| Ex. | R$_1$ | R$_2$ | R$_3$ | X$_1$ | X$_2$ |
| --- | --- | --- | --- | --- | --- |
| 3-1 | CH$_3$(CH$_2$)$_8$ | (CH$_2$)$_9$CH$_3$ | H | CH$_2$ | O |
| 3-2 | CH$_3$(CH$_2$)$_5$ | (CH$_2$)$_7$CH$_3$ | 3'-CN | CH$_2$ | S |
| 3-3 | CH$_3$(CH$_2$)$_{15}$ | (CH$_2$)$_3$CH$_3$ | 2'-F | O | O |
| 3-4 | CH$_3$CH$_2$C*H(CH$_3$)CH$_2$ | (CH$_2$)$_5$CH$_3$ | 3'-NO$_2$ | S | O |
| 3-5 | CH$_3$(CH$_2$)$_5$ | CH$_3$(CH$_2$)$_8$ | H | CH$_2$ | CH$_2$ |
| 3-6 | C$_5$H$_{11}$CFCH$_3$ | C$_{10}$H$_{21}$ | H | COO | O |
| 3-7 | C$_8$H$_{17}$ | C$_5$H$_{11}$ | 2'-F, 3'-F | O | — |

EXAMPLE 4

The procedure of Example 2 was repeated to prepare liquid crystalline compounds represented by the general formula (II) wherein R$_1$, R$_2$, R$_3$, X$_1$, X$_2$, and Z represent respective groups specified in Table 2. All the liquid crystalline compounds thus obtained had the same properties as the liquid crystalline compound prepared in Example 2.

TABLE 2

| Ex. | $R_1$ | $R_2$ | $R_3$ | $X_1$ | $X_2$ | Z |
|---|---|---|---|---|---|---|
| 4-1 | $CH_3(CH_2)_8$ | $(CH_2)_9CH_3$ | 2',3'-F | $CH_2$ | O | CH=N |
| 4-2 | $CH_3(CH_2)_5$ | $(CH_2)_7CH_3$ | 3'-CN | $CH_2$ | S | COO |
| 4-3 | $CH_3CH_2C^*H(CH_3)CH_2$ | $(CH_2)_5CH_3$ | 3'-$NO_2$ | $CH_2$ | O | CH=CH |
| 4-4 | $CH_3(CH_2)_{15}$ | $(CH_2)_3H_3$ | H | O | O | C≡C |
| 4-5 | $CH_3(CH_2)_8$ | $CH_3(CH_2)_8$ | H | $CH_2$ | $CH_2$ | N=N |
| 4-6 | $C_4H_9$ | $C_6H_5$—$C_4H_9$ | H | — | COO | OCO |
| 4-7 | $C_2H_5CH(CH_3)CH_2$ | $C_{10}H_{21}$ | H | OOC | O | CO |
| 4-8 | $C_6H_{13}OC_6H_5$ | H | H | CH=N | — | CH=N |

EXAMPLE 5

Two glass substrates each having an ITO electrode (surface electric resistance: 100–200 Ω/□) provided by vacuum film formation were laminated onto each other so that the ITO electrodes faced each other while providing a gap (about 2 μm) therebetween using spacer particles, thereby preparing a cell. The naphthalene compound liquid crystal (2-(4'-octylphenyl)-6-dodecyloxynaphthalene, Crystal—79° C.—SmX—121° C.—Iso.) prepared in Example 1 was mixed with 1% by mole of a luminescent dye (3-(2-benzothiazolyl)-7-(diethylamino)-2H-1-benzopyran-2-one (manufactured by Nihon Kanko Shikiso Kenkyusho (Japan Photosensitive Dye Laboratory), oscillating wavelength: 507–585 nm), and the mixture was poured at 125° C. into the cell. An d.c. electric field of 250 V was applied to the cell in a dark place. As a result, light emission derived from the fluorescent wavelength of the fluorescent dye was observed.

As described above, the present invention can provide novel liquid crystalline compounds having not only liquid crystallinity but also charge transport capability. The novel liquid crystalline compounds can be used in applications, where the conventional liquid crystalline compounds are used, and, in addition, are useful as materials for optical sensors, electroluminescence devices, photoconductors, space light modulating device, thin film transistors, other sensors and the like, utilizing the charge transfer capability. In particular, some of the liquid crystalline compounds of the present invention have both electron transport capability and hole transport capability and, when mixed with a fluorescent material in order to use it as a material for an electroluminescence device, can provide luminescence.

What is claimed is:

1. A process for producing a liquid crystalline compound, represented by the following general formula (II):

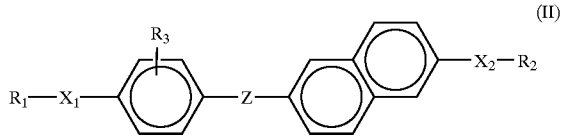

wherein $R_1$ and $R_2$ each independently represent a straight-chain, branched or cyclic, saturated or unsaturated hydrocarbon group having 1 to 22 carbon atoms and may be attached directly to the aromatic ring without through $X_1$ or $X_2$; $R_3$ represents a hydrogen atom, a cyano group, a nitro group, or a methyl group; $X_1$ represents a sulfur atom, or a —CO—, —OCO—, —COO—, —N=CH—, —CONH—, —NH—, or —CH$_2$— group; $X_2$ represents an oxygen atom, a sulfur atom, or a —CO—, —CO—, —COO—, —N=CH—, —CONH—, —NH—, —NHCO—, or —CH$_2$— group; and Z represents a —N=N—, —CH=N—, —CH$_2$S—, or —CH=CH— group comprising the step of reacting a compound represented by the following general formula (3) with a compound represented by the following general formula (4):

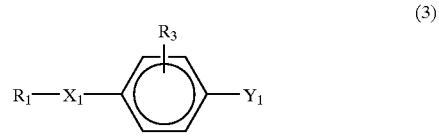

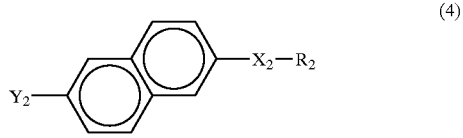

wherein $R_1$, $R_2$, $R_3$, $X_1$, and $X_2$ are as defined above; and $Y_1$ and $Y_2$ are respectively groups which are reacted with each other to form a —COO—, —OCO—, —N=N—, —CH=N—, —CH$_2$S—, —CH=CH—, or —C≡C— group.

2. An image display device comprising a liquid crystalline compound represented by the following general formula (II):

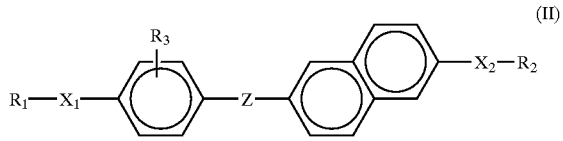

wherein $R_1$ and $R_2$ each independently represent a straight-chain, branched or cyclic, saturated or unsaturated hydrocarbon group having 1 to 22 carbon atoms and may be attached directly to the aromatic ring without through $X_1$ or $X_2$; $R_3$ represents a hydrogen atom, a cyano group, a nitro group, or a methyl group; $X_1$ represents a sulfur atom, or a —CO—, —OCO—, —COO—, —N=CH—, —CONH—, —NH—, or —CH$_2$— group; $X_2$ represents an oxygen atom, a sulfur atom, or a —CO—, —OCO—, —COO—, —N=CH—, —CONH—, —NH—, —NHCO—, or —CH$_2$— group; and Z represents a —N=N—, —CH=N—, —CH$_2$S—, or —CH=CH— group in a drive path.

3. An electroluminescence device comprising a liquid crystalline compound represented by the following general formula (II):

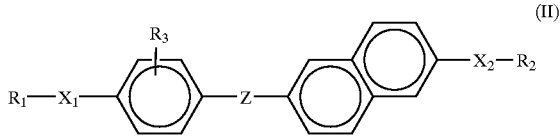

wherein $R_1$ and $R_2$ each independently represent a straight-chain, branched or cyclic, saturated or unsaturated hydrocarbon group having 1 to 22 carbon atoms and may be attached directly to the aromatic ring without through $X_1$ or $X_2$; $R_3$ represents a hydrogen atom, a cyano group, a nitro group, or a methyl group; $X_1$ represents a sulfur atom, or a —CO—, —OCO—, —COO—, —N=CH—, —CONH—, —NH—, or —CH$_2$— group; $X_2$ represents an oxygen atom, a sulfur atom, or a —CO—, —OCO—, —COO—, —N=CH—, —CONH—, —NH—, —NHCO—, or —CH$_2$— group; and Z represents a —N=N—, —CH=N—, —CH$_2$S—, or —CH=CH— group in a drive path.

4. A photoconductor comprising a liquid crystalline compound represented by the following general formula (II):

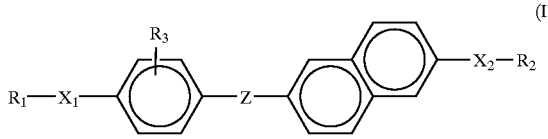

wherein $R_1$ and $R_2$ each independently represent a straight-chain, branched or cyclic, saturated or unsaturated hydrocarbon group having 1 to 22 carbon atoms and may be attached directly to the aromatic ring without through $X_1$ or $X_2$; $R_3$ represents a hydrogen atom, a cyano group, a nitro group, or a methyl group; $X_1$ represents a sulfur atom, or a —CO—, —OCO—, —COO—, —N=CH—, —CONH—, —NH—, or —CH$_2$— group; $X_2$ represents an oxygen atom, a sulfur atom, or a —CO—, —OCO—, —COO—, —N=CH—, —CONH—, —NH—, —NHCO—, or —CH$_2$— group; and Z represents a —N=N—, —CH=N—, —CH$_2$S—, or —CH=CH— group in a drive path.

5. A space light modulating device comprising a liquid crystalline compound represented by the following general formula (II):

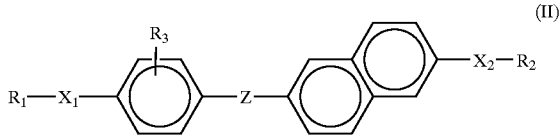

wherein $R_1$ and $R_2$ each independently represent a straight-chain, branched or cyclic, saturated or unsaturated hydrocarbon group having 1 to 22 carbon atoms and may be attached directly to the aromatic ring without through $X_1$ or $X_2$; $R_3$ represents a hydrogen atom, a cyano group, a nitro group, or a methyl group; $X_1$ represents a sulfur atom, or a —CO—, —OCO—, —COO—, —N=CH—, —CONH—, —NH—, or —CH$_2$— group; $X_2$ represents an oxygen atom, a sulfur atom, or a —CO—, —OCO—, —COO—, —N=CH—, —CONH—, —NH—, —NHCO—, or —CH$_2$— group; and Z represents a —N=N—, —CH=N—, —CH$_2$S—, or —CH=CH— group in a drive path.

6. A thin film transistor comprising a liquid crystalline compound represented by the following general formula (II):

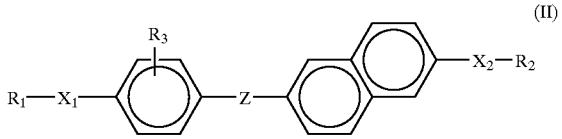

wherein $R_1$ and $R_2$ each independently represent a straight-chain, branched or cyclic, saturated or unsaturated hydrocarbon group having 1 to 22 carbon atoms and may be attached directly to the aromatic ring without through $X_1$ or $X_2$; $R_3$ represents a hydrogen atom, a cyano group, a nitro group, or a methyl group; $X_1$ represents a sulfur atom, or a —CO—, —OCO—, —COO—, —N=CH—, —CONH—, —NH—, or —CH$_2$— group; $X_2$ represents an oxygen atom, a sulfur atom, or a —CO—, —OCO—, —COO—, —N=CH—, —CONH—, —NH—, —NHCO—, or —CH$_2$— group; and Z represents a —N=N—, —CH=N—, —CH$_2$S—, or —CH=CH— group in a drive path.

7. A sensor comprising a liquid crystalline compound represented by the following general formula (II):

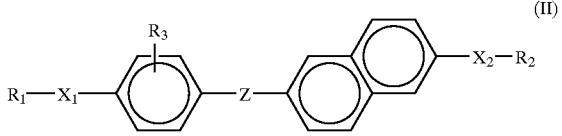

wherein $R_1$ and $R_2$ each independently represent a straight-chain, branched or cyclic, saturated or unsaturated hydrocarbon group having 1 to 22 carbon atoms and may be attached directly to the aromatic ring without through $X_1$ or $X_2$; $R_3$ represents a hydrogen atom, a cyano group, a nitro group, or a methyl group; $X_1$ represents a sulfur atom, or a —CO—, —OCO—, —COO—, —N=CH—, —CONH—, —NH—, or —CH$_2$— group; $X_2$ represents an oxygen atom, a sulfur atom, or a —CO—, —OCO—, —COO—, —N=CH—, —CONH—, —NH—, —NHCO—, or —CH$_2$— group; and Z represents a —N=N—, —CH=N—, —CH$_2$S—, or —CH=CH— group in a drive path.

8. An image display device comprising a liquid crystalline compound having charge transport capability and represented by the following general formula (II):

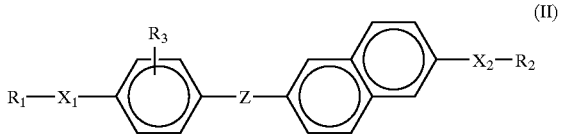

wherein $R_1$ and $R_2$ each independently represent a straight-chain, branched or cyclic, saturated or unsaturated hydrocarbon group having 1 to 22 carbon atoms and may be attached directly to the aromatic ring without through $X_1$ or $X_2$; $R_3$ represents a hydrogen atom, a cyano group, a nitro group, or a methyl group; $X_1$ represents a sulfur atom, or a —CO—, —OCO—, —COO—, —N=CH—, —CONH—, —NH—, or —CH$_2$— group; $X_2$ represents an oxygen atom, a sulfur atom, or a —CO—, —OCO—, —COO—, —N=CH—, —CONH—, —NH—, —NHCO—, or —CH₂— group; and Z represents a —N=N—, —CH=N—, —CH₂S—, or —CH=CH— group in a drive path.

9. An electroluminescence device comprising a liquid crystalline compound having charge transport capability and represented by the following general formula (II):

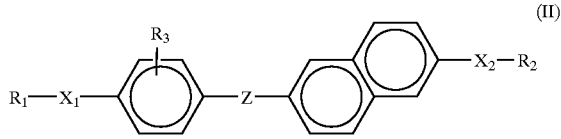

wherein R₁ and R₂ each independently represent a straight-chain, branched or cyclic, saturated or unsaturated hydrocarbon group having 1 to 22 carbon atoms and may be attached directly to the aromatic ring without through X₁ or X₂; R₃ represents a hydrogen atom, a cyano group, a nitro group, or a methyl group; X₁ represents a sulfur atom, or a —CO—, —OCO—, —COO—, —N=CH—, —CONH—, —NH—, or —CH₂— group; X₂ represents an oxygen atom, a sulfur atom, or a —CO—, —OCO—, —COO—, —N=CH—, —CONH—, —NH—, —NHCO—, or —CH₂— group; and Z represents a —N=N—, —CH=N—, —CH₂S—, or —CH=CH— group in a drive path.

10. A photoconductor comprising a liquid crystalline compound having charge transport capability and represented by the following general formula (II):

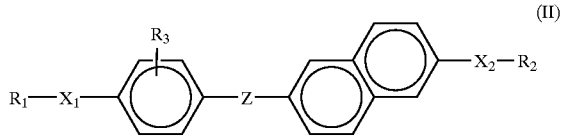

wherein R₁ and R₂ each independently represent a straight-chain, branched or cyclic, saturated or unsaturated hydrocarbon group having 1 to 22 carbon atoms and may be attached directly to the aromatic ring without through X₁ or X₂; R₃ represents a hydrogen atom, a cyano group, a nitro group, or a methyl group; X₁ represents a sulfur atom, or a —CO—, —OCO—, —COO—, —N=CH—, —CONH—, —NH—, or —CH₂— group; X₂ represents an oxygen atom, a sulfur atom, or a —CO—, —OCO—, —COO—, —N=CH—, —CONH—, —NH—, —NHCO—, or —CH₂— group; and Z represents a —N=N—, —CH=N—, —CH₂S—, or —CH=CH— group in a drive path.

11. A space light modulating device comprising a liquid crystalline compound having charge transport capability and represented by the following general formula (II):

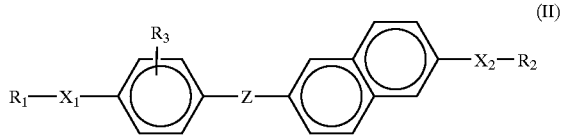

wherein R₁ and R₂ each independently represent a straight-chain, branched or cyclic, saturated or unsaturated hydrocarbon group having 1 to 22 carbon atoms and may be attached directly to the aromatic ring without through X₁ or X₂; R₃ represents a hydrogen atom, a cyano group, a nitro group, or a methyl group; X₁ represents a sulfur atom, or a —CO—, —OCO—, —COO—, —N=CH—, —CONH—, —NH—, or —CH₂— group; X₂ represents an oxygen atom, a sulfur atom, or a —CO—, —OCO—, —COO—, —N=CH—, —CONH—, —NH—, —NHCO—, or —CH₂— group; and Z represents a —N=N—, —CH=N—, —CH₂S—, or —CH=CH— group in a drive path.

12. A thin film transistor comprising a liquid crystalline compound having charge transport capability and represented by the following general formula (II):

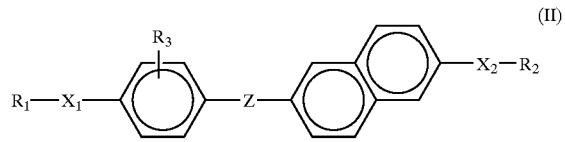

wherein R₁ and R₂ each independently represent a straight-chain, branched or cyclic, saturated or unsaturated hydrocarbon group having 1 to 22 carbon atoms and may be attached directly to the aromatic ring without through X₁ or X₂; R₃ represents a hydrogen atom, a cyano group, a nitro group, or a methyl group; X₁ represents a sulfur atom, or a —CO—, —OCO—, —COO—, —N=CH—, —CONH—, —NH—, or —CH₂— group; X₂ represents an oxygen atom, a sulfur atom, or a —CO—, —OCO—, —COO—, —N=CH—, —CONH—, —NH—, —NHCO—, or —CH₂— group; and Z represents a —N=N—, —CH=N—, —CH₂S—, or —CH=CH— group in a drive path.

13. A sensor comprising a liquid crystalline compound having charge transport capability and represented by the following general formula (II):

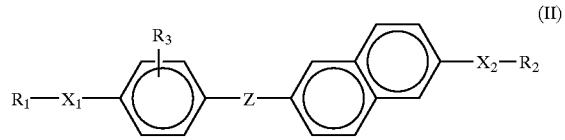

wherein R₁ and R₂ each independently represent a straight-chain, branched or cyclic, saturated or unsaturated hydrocarbon group having 1 to 22 carbon atoms and may be attached directly to the aromatic ring without through X₁ or X₂; R₃ represents a hydrogen atom, a cyano group, a nitro group, or a methyl group; X₁ represents a sulfur atom, or a —CO—, —OCO—, —COO—, —N=CH—, —CONH—, —NH—, or —CH₂— group; X₂ represents an oxygen atom, a sulfur atom, or a —CO—, —OCO—, —COO—, —N=CH—, —CONH—, —NH—, —NHCO—, or —CH₂— group; and Z represents a —N=N—, —CH=N—, —CH₂S—, or —CH=CH— group in a drive path.

* * * * *